United States Patent [19]

Liefke et al.

[11] Patent Number: 4,900,252
[45] Date of Patent: Feb. 13, 1990

[54] RECOGNITION SYSTEM FOR TOOLS INSERTABLE INTO DENTAL TREATMENT INSTRUMENTS

[75] Inventors: Johannes Liefke, Bensheim; Bernd Nickel, Lorsch; Josef Pabst, Heddesheim; Otto Fleer, Bensheim, all of Fed. Rep. of Germany

[73] Assignee: Siemens Aktiengesellschaft, Berlin and Munich, Fed. Rep. of Germany

[21] Appl. No.: 217,716

[22] Filed: Jul. 11, 1988

[30] Foreign Application Priority Data

Jul. 24, 1987 [DE] Fed. Rep. of Germany ....... 3724586
Apr. 22, 1988 [DE] Fed. Rep. of Germany ....... 3813714

[51] Int. Cl.⁴ ............................ A61C 1/00; A61C 3/00
[52] U.S. Cl. ................................ 433/27; 364/413.28; 433/98
[58] Field of Search ................ 433/27, 28, 98, 101, 433/105; 364/413.28

[56] References Cited

U.S. PATENT DOCUMENTS 4,305,126 12/1981 Beier ............................. 364/413.28
4,571,681 2/1986 Beier et al. ..................... 433/28

FOREIGN PATENT DOCUMENTS

212182 8/1984 Fed. Rep. of Germany .
3447639 7/1986 Fed. Rep. of Germany ........ 433/27
1419622 12/1975 United Kingdom .
2032154 4/1980 United Kingdom .................. 433/28
2027920 12/1980 United Kingdom .

*Primary Examiner*—Cary E. Stone
*Attorney, Agent, or Firm*—Hill, Van Santen, Steadman & Simpson

[57] ABSTRACT

A recognition system is provided for tools, such as drill bits and milling bits, which are insertable into dental treatment instruments, each of the tools having an optimum speed at which the tool must be rotated for effective treatment. In the recognition system, each tool is provided with a code corresponding to the speed or speed graduation necessary to effectively use the tool. The system also includes a reader which reads the code on each tool, and generates identifying signals in accordance with the code, which are supplied to an evaluation logic. The logic converts the signal from the reader into control signals for the drive motor used to operate the tool, as well as indicator signals for visually displaying information relating to the tool currently in use.

37 Claims, 6 Drawing Sheets

| Tool Group | Tool RPM | Code | Transmission Ratio | | Motor RPM | Motor RPM in % |
|---|---|---|---|---|---|---|
| | | | Head | Sleeve | | |
| 0 | 400 | 0000 | 1:1 | 20:1 | $8 \cdot 10^3$ | 20 |
| I | 600 | 0001 | 1:1 | 20:1 | $12 \cdot 10^3$ | 30 |
| | 800 | 0010 | 1:1 | 20:1 | $16 \cdot 10^3$ | 40 |
| | 1000 | 0100 | 1:1 | 20:1 | $20 \cdot 10^3$ | 60 |
| | 1500 | 1000 | 1:1 | 20:1 | $30 \cdot 10^3$ | 80 |
| II | $2 \cdot 10^3$ | 0011 | 1:1 | 4:1 | $8 \cdot 10^3$ | 20 |
| | $4 \cdot 10^3$ | 0110 | 1:1 | 4:1 | $16 \cdot 10^3$ | 40 |
| | $6 \cdot 10^3$ | 0101 | 1:1 | 4:1 | $24 \cdot 10^3$ | 60 |
| | $10 \cdot 10^3$ | 1100 | 1:1 | 4:1 | $40 \cdot 10^3$ | 100 |
| | $20 \cdot 10^3$ | 1001 | 1:1 | 1:1 | $20 \cdot 10^3$ | 60 |
| III | $30 \cdot 10^3$ | 0111 | 1:1 | 1:3 | $10 \cdot 10^3$ | 20 |
| | $50 \cdot 10^3$ | 1011 | 1:1 | 1:3 | $17 \cdot 10^3$ | 40 |
| | $70 \cdot 10^3$ | 1101 | 1:1 | 1:3 | $23 \cdot 10^3$ | 60 |
| | $100 \cdot 10^3$ | 1110 | 1:1 | 1:3 | $33 \cdot 10^3$ | 80 |
| IV | $160 \cdot 10^3$ | 1111 | 1:1.33 | 1:3 | $40 \cdot 10^3$ | 100 |

RECOGNITION SYSTEM FOR TOOLS INSERTABLE INTO DENTAL TREATMENT INSTRUMENTS

BACKGROUND OF THE INVENTION

1. Field of the Invention

The present invention is directed to a recognition system for tools insertable into a dental treatment instruments wherein the various tools available for insertion are removeably stored in a tool holder or magazine, with each tool having a different optimum rotational speed for most effective use of the tool.

2. Description of the Prior Art

Approximately 50 different tools in the form of drill bits or milling bits are available for use by a dentist for the purpose of drilling, polishing, grinding and milling procedures. Moreover, dentists also have a further plurality of specialized tools for unique treatments, such tools having, for example, a specialized size adapted for the particular treatment.

Primarily on the basis of its chip removal characteristic, each tool has an optimum speed or speed range for most effective use of the tool. Recommendations for a specific speed range are set forth in the catalogues of the tool manufacturers. The dentist using such a variety of tools has drive systems available by which the most beneficial speed for operating a selected tool can be set. The actual tool speed can be set by varying the drive speed of the drive motor and/or by varying the transmission ratio of the gearing between the drive motor and the tool itself. Such treatment instruments can be completely self-contained, sometimes referred to as hand pieces or angle pieces, or may be treatment heads which are put in place on a larger drive element.

Assistance in the selection of the optimum speed associated with a particular tool is provided by tool magazines known in the prior art, such as U.S. Pat. No. 4,305,126 and United Kingdom specification No. 2 047 920, wherein the various tools (bits) are arranged at specific locations in a tool magazine, with each location in the tool magazine having an address and having parameters associated with that address such as speed, cutting rate and the like. When a tool is removed from a receptacle, the address associated with that receptacle, and thus with the tool, is forwarded to a central control which displays the relevant parameters on a screen.

Such known systems have the disadvantage that the information is associated with the receptacle in the magazine, and thus requires a correct matching of the tool with that receptacle be maintained, i.e., the same tool must always be returned to the same location after use. Errors in returning a tool to the wrong location can occur, thus resulting in incorrect data being displayed for that tool the next time it is used.

SUMMARY OF THE INVENTION

It is an object of the present invention to provide a recognition system for tools insertable into dental treatment instruments which provides an unambigious control of the drive system for the tool so that the tool is always operated at the proper speed.

It is a further object of the present invention to provide such a system which additionally unambigiously displays the correct operating information associated with a selected tool.

The above objects are achieved in accordance with the principles of the present invention in a tool recognition system wherein the tools are provided with a coding, such as in the form of a series of circumferential lines, the coding identifying different speeds or speed graduations associated with the proper operation of the tool. A reader for reading the coding is provided which supplies information relating to the tool parameters to evaluation logic, which in turn generates signals for controlling the drive motor to be used for operating the tool as well as signals for visual display identifying the particular drive motor to be used with the tool and any gearing sleeves which must be put in place for effective use of the tool. A display having a symbolic representation for various treatment instruments may be provided, wherein the treatment instrument is visually displayed in accordance with the coding of the selected tool. Upon selection of an arbitrary tool provided with such coding, the user is thus informed of the treatment instrument associated with the selected tool. Instead of a symbolic, i.e., graphic, representation, a text display may be provided, or a voice description of the tool may be provided.

As noted above, the treatment instrument may be a treatment head which directly accepts the selected tool, or may be a gearing sleeve disposed between the treatment head and the drive motor, with different gearing sleeves being available for use having different transmission ratios to achieve a step-down or step-up of the motor rpm.

The coding on the tool is preferably a binary code system. One or more sensor elements, such as opto-electronic sensor elements, can be provided for reading the coding information. As stated above, the coding may be in the form of lines on the tool, forming a bar code. The lines may be in the form of rings extending around the entire circumference of the tool, or may proceed parallel to the axis is the tool shank. Markings may also be provided on the side of the tool facing away from the tool tip.

The tool speeds are divided into a plurality of steps within freely selectable minimum and maximum speeds. Reading of the line markings is preferably undertaken such that, given the presence of a marking, this location in the reading system is assigned a binary "one". In the event of a faulty reading, this system has the advantage that a lower speed range or a lower speed will be automatically set, so that a higher speed than is optimally necessary can never be set.

Reading of the markings can be undertaken opto-electronically or magnetically. The reader is preferably allocated to the storage locations for the tools in the magazine, however, if structural conditions permit, the reader may be directly allocated to the treatment instrument. In the latter instance, for example, the clamping arrangement which accepts and holds the tool in the treatment head can be provided with the reader, whose signals are conducted to the evaluation logic and display unit, which may be arranged to the side of the apparatus. These signals can be conducted via separate lines in the hand piece, or by other transmission means such as infrared radiators.

In a further embodiment of the invention, a second coding can be provided in the region of the tool acceptance sleeve (the clamping arrangement or the tool drive shaft) with the identifying signals from the second coding being used in a rated value/actual value comparison in a second reader. The rated value is formed by the identifying signals from the tool coding. The drive motor is switched on and its rotational speed is increased until the rated and actual values coincide, on the basis of the rated value/actual value comparison.

The value identified in this manner can then be stored, and when the same drive unit and tool are again used in combination, the motor speed will automatically set or limited, thus limiting the maximum possible speed of the tool.

The second coding can also the magnetic or optical. The shaft end or clamping arrangement into which the tool shank is inserted can be cross-magnetized, or provided with optical markings at its tool-engagement end.

One marking or a plurality of markings can be disposed at the tool-engagement end or at the circumference of the shaft or clamping arrangement, so that information regarding the speed, or a multiple of the speed, can be derived therefrom. The markings may again be coded, for example in the form of asymmetrically arranged markings, to permit these markings to be read only with a special reader. This special reader may be integrated in the housing with the first reader.

DESCRIPTION OF THE PREFERRED EMBODIMENTS

Figure 1:
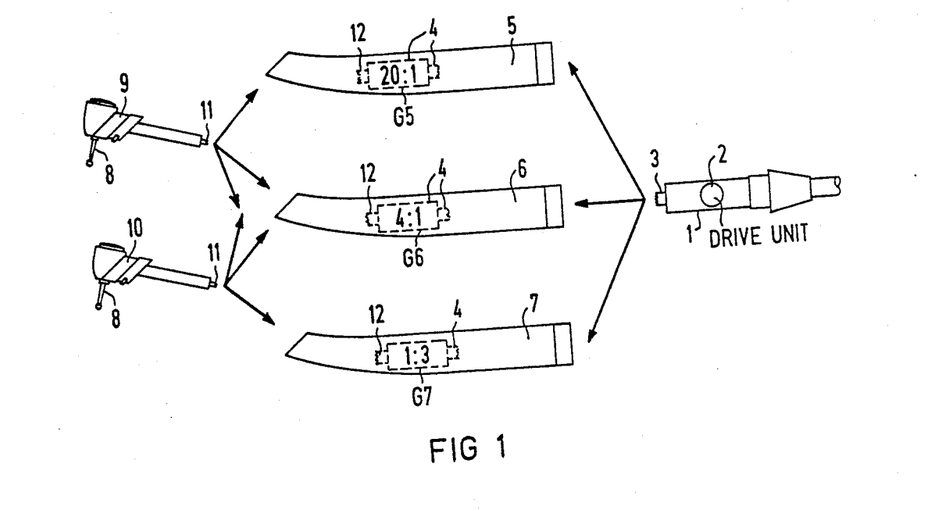
FIG. 1 is a schematic showing of a dental drive system with a plurality of treatment instruments, showing the various combinations thereof.

A simplified illustration of a dental tool drive system is shown in FIG. 1. The system includes a drive unit 1 which contains a drive motor 2 (such as an electric motor or a pneumatic motor) with a driveshaft 3 coupled to one end 4 of one of a plurality of gear sleeves 5, 6 or 7. The gear sleeves 5, 6 and 7 have identical exteriors, and differ internally only by having respectively different gearing cartridges. For example, a gearing cartridge G5 for the gearing sleeve 5 may have a transmission ratio of 20:1, a gearing cartridge G6 in the gearing sleeve 6 may have a transmission ratio of 4:1, and a gearing cartridge G7 in the gearing sleeve 7 may have a transmission ratio of 1:3, i.e., a step-down. One of a plurality of treatment heads, such as heads 9 or 10, each accepting a tool 8 in a known manner, can be attached to one of the gearing sleeves 5, 6 or 7. The treatment heads 9 and 10 also have respectively different transmission ratios. For example, the treatment head 9 may have a direct transmission ratio of 1:1, whereas the treatment head 10 may have a step-down ratio of 1:3. The treatment heads 9 and 10 can be optionally placed on one of the gearing sleeves 5, 6 or 7, so that various combinations of step-down and step-up ratios can be achieved. Each drive head 9 and 10 has an end 11 which is coupled to an end 12 of the gearing sleeve which is used in combination therewith.

Figure 5:
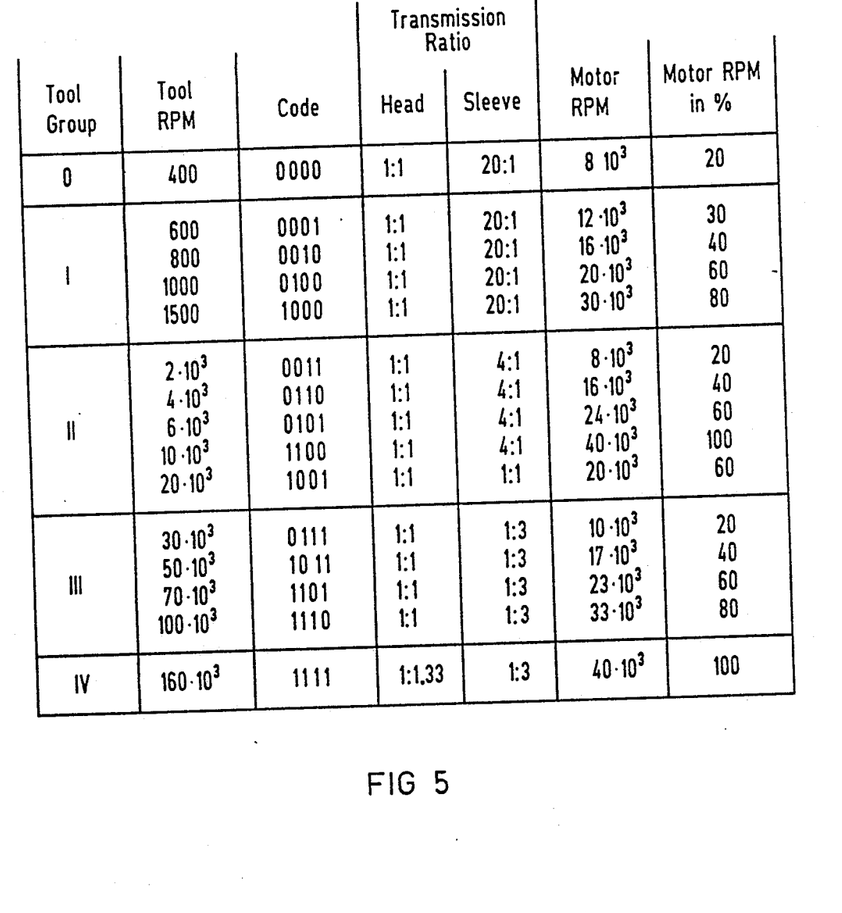
FIG. 5 is a table showing the speeds allocated to the various tools shown in FIG. 4.

It is assumed that the drive motor 2 is of the standard type which can be controlled in a range between 8,000 rpm and 40,000 rpm. An actual tool speed between 400 rpm and 160,000 rpm can thus be achieved, depending upon the combination of gearing sleeve and treatment head which is used. A table showing the various speed ranges available is shown in FIG. 5.

When not being used, a tool 8 is held in one of receptacle locations 13 or 14, together with other tools referenced 8′, 8″ etc., which differ in view of the working element (such as drilling or polishing or grinding tools), but have identically fashioned shanks. In the simplest case, the receptacle locations 14 can simply be depressions corresponding to the shape of the tool shank in which the tools 8, 8′, 8″ etc. can be arbitrarily placed. The receptacle locations 14 can be a part of a magazine 15, or can be separate containers, or any other suitable storage means.

In contrast to the receptacle locations 14, which have no function beyond receiving and holding the various tools, the receptacle location 13 is a special single-tool receptacle location in which an arbitrary tool, taken from one of the receptacle locations 14, can be introduced for recognition of the operation parameters allocated thereto.

Figure 2:
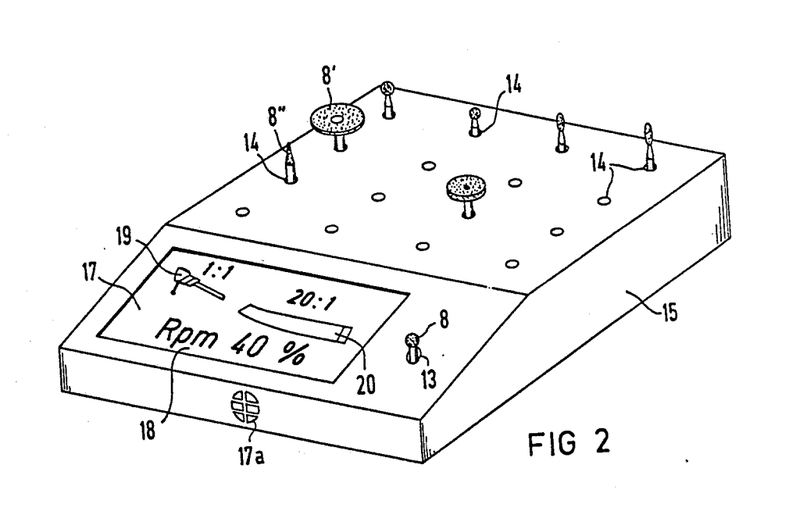
FIG. 2 is a perspective view of a magazine of the type suitable for use in a system in accordance with the principles of the present invention for storing various tools and providing an integrated display.

For this purpose, the magazine 15 is provided with a display screen 17 on which an indication 18 of the speed of the drive motor can be visually displayed digitally and in a percentage, together with graphic representations 19 and 20 respectively showing the treatment head and the gearing sleeve which are to be used with the selected tool.

Depending upon the tool introduced into the receptacle location 13, the motor speed (position 18 in FIG. 2) allocated to this tool is optically displayed on the screen 17 together with the gearing sleeve and treatment head matched to the selected tool. After introducing an arbitrarily selected tool into the receptacle 13, the user is therefore immediately informed as to which of the gearing sleeves 5 through 7 is to be used and which of the treatment heads 9 or 10 is to be used in combination with the selected tool. In the embodiment shown in FIG. 2, the gearing sleeve 5 having the transmission ratio of 20:1 and the treatment head 9 having a direct transmission of 1:1 are indicated as those which are to be used in combination with the tool 8.

Figure 4:
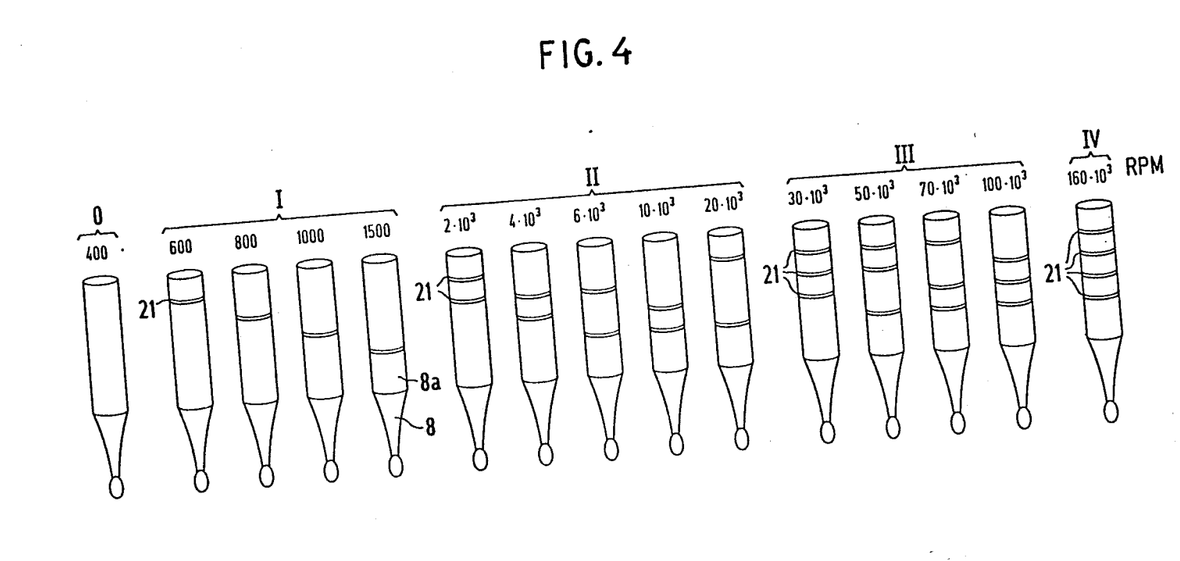
FIG. 4 shows the various types of coding which can be applied to different tools in accordance with the principles of the present invention.

Assuming that a defined speed or a defined speed range can be allocated to each tool, the overall tool speed range from 400 rpm through 160,000 rpm can be divided into, for example, five tool groups (0 through IV), as shown in FIGS. 4 and 5. Group 0 contains tools, for example, which are only suitable for speeds up to 400 rpm, Group I contains tools operable at speeds in graduations of 600, 800, 1,000 and 1,500 rpm, Group II includes tools having speeds between 2,000 rpm and 20,000 rpm, Group III includes tools operated at speeds between 30,000 rpm and 100,000 rpm, and Group IV includes tools to be operated at speeds of 160,000 rpm or above. This subdivision can be arbitrarily selected; in the exemplary embodiment it has been assumed that the tools of Group 0 have no coding, but the tools of Groups I through IV are provided with a coding. This subdivision has the advantage that tools which are already commercially available, and which have no coding of any type, are always operated at the lowest speeds for safety reasons.

Coding is undertaken using a binary code (yes/no) and is preferably in the form of bar markings which are applied to the shank 8a of the tool. The markings may be applied transversely relative to the longitudinal axis of the tool, such as the markings 21 shown in FIGS. 3 and 4, or may be applied parallel to the longitudinal axis of the tool, as shown by the markings 30 in FIG. 6. One marking is used to identify the tools in Group I, two markings (bars) are used to identify the tools in Group II, three markings (bars) are provided for tools in Group III, and four markings are provided for the tools in Group IV. The markings, such as the rings 21, can be applied to the shank 8a of the tool by etching or laser-burning. Other types of coding, such as magnetic strips or the like, are possible, however, optically recognizable markings have the advantage that the user can visually perceive the markings as well, and thus can have a general indication of the speed at which the tool should be operated when the user removes the tool from one of the receptacles 14. As can be seen in FIG. 4, the markings 21 can be equally spaced along the tool shank. The optically recognizable lines or bars preferably correspond to a "one" in the binary coding system, whereas empty fields correspond to a binary "zero." This arrangement has the advantage that the next-lowest speed or next-lowest speed range will be automatically indicated or set given an incorrect reading.

Figure 3:
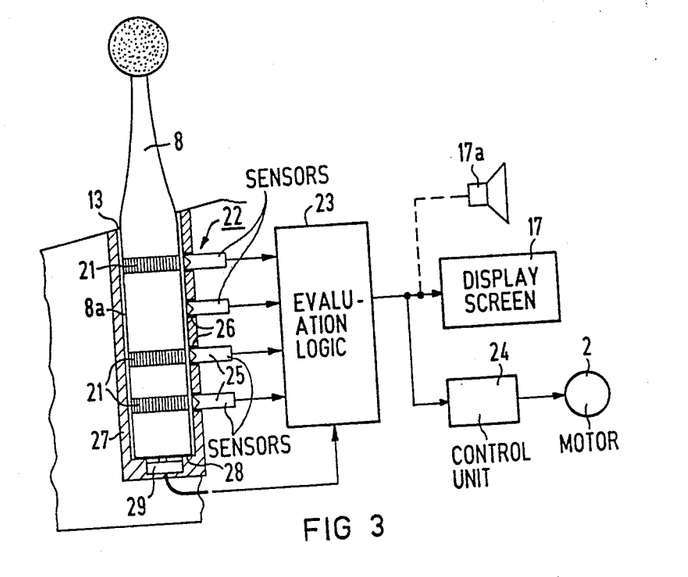
FIG. 3 is a schematic block diagram of a reader in accordance with the principles of the present invention.

The coding applied to the tool shank is read by a reader 22, and the data obtained thereby are supplied to evaluation logic 23, which converts the incoming signals to outgoing signals in a form adapted to operate the display 17 and/or to be used by a control unit 24 for the drive motor 2.

As shown in FIG. 3, the reader 22 has a plurality, such as four, opto-electronic sensors 25, such as focused reflex light barriers (bar code readers) which are arranged one above the other in respective recesses 26 of a sleeve 27 for the receptacle location 13. The sensors 25 are disposed at those locations along the receptacle 13 which correspond to the locations of the markings 21 when the shank 8a is fully inserted in the receptacle 13. Full insertion is determined by a microswitch 29 provided in a recess 28 at the bottom of the sleeve 27, which forwards a signal to the evaluation logic 23 when actuated, thereby initiating reading of the coding.

The signals acquired from the coded information from the sensors 25 are processed in the evaluation logic 23 in accordance with the table shown in FIG. 5. In the exemplary embodiment of FIG. 3, the sensors 25 would read a code 1011 which would provide a display on the screen 17 identifying that the treatment head 9 having the direct transmission ratio of 1:1 and the gearing sleeve 7 having the step-down ratio of 1:3 should be used, so that, given a motor speed of 17,000 rpm, a tool rotational speed of 50,000 rpm is achieved. The motor speed of 17,000 rpm may be indicated as a percentage, such as 40%, of the maximum motor speed.

Instead of using a plurality of sensor elements as shown in FIG. 3, it is also possible in the context of the present invention to provide only a single sensor element, and to use a different type of reader. Using the ring markings 21 as shown in FIGS. 3 and 4, the single sensor element could be disposed in the upper region of the receptacle sleeve 27, and the coding could be serially read as the tool shank 8a is introduced up to the microswitch 29.

Figure 6:
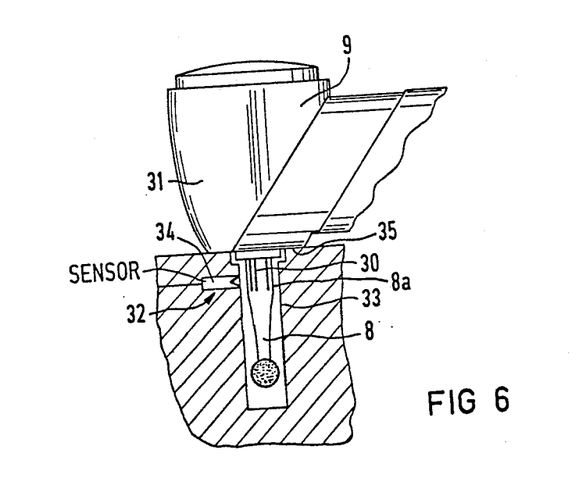
FIG. 6 shows a further embodiment of a reader in accordance with the principles of the present invention.

It is also possible to use a single sensor element in an embodiment wherein the markings proceed parallel to the tool axis, as shown in FIG. 6. In this embodiment the shank 8a has markings 30 which projects out of the tool head housing 31 to such an extent, when the tool is inserted in the treatment head 9 (or 10) that at least a portion of the markings 30 are within the field of view of the reader, generally referenced at 32. The reader 32 can e part of a single-tool receptacle location 33 constructed in a manner similar to that shown in FIG. 3, but having only one opto-electronic sensor element 34, disposed in the upper region thereof. The sensor element 34 is disposed so that at least a portion of the markings 30 are in registry therewith when the housing 31 of the treatment head 9 (or 10) is placed above the receptacle 33. Reading of the coded information can ensue by turning either the treatment head 9 (or 10) or by turning the tool receptacle location 33. A defined detent 35 is provided indicating proper seating of the housing 31 against the upper surface of the receptacle 33 to ensure proper positioning of the markings 30 relative to the sensor 34 before reading can be initiated.

The symbolic representation of the components as shown in FIG. 2 can be replaced by a textual identification of the components based on the data acquired by reading in the above-described manner, or such information can be generated by a voice output. For this purpose, as shown in FIG. 2, the magazine 15 may be provided with a grill for a speaker 17a, the speaker 17a being provided with signals from the evaluation logic 23, as shown in FIG. 3.

A further embodiment of the invention is shown in FIGS. 7 through 14. In the embodiment described heretofore, it has been assumed that the treatment head or the gearing sleeve which is indicated on the display screen 17 is actually used by the user. In the embodiment shown in FIGS. 7 through 14, the drive speed of the tool can be controlled or limited directly dependent on the tool which is used, regardless of which combination of treatment head and gearing sleeve are used.

Figure 7:
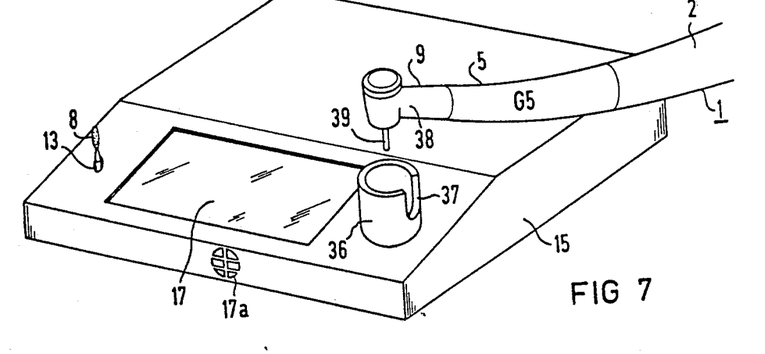
FIG. 7 is a perspective view of a further embodiment of a tool magazine constructed in accordance with the principles of the present invention having a treatment instrument receptacle.

In the embodiment shown in FIG. 7, in addition to the receptacle location 13 for the selected tool 8, the magazine 15 includes a treatment head receptacle 36 adapted to receive one of the treatment heads 9 or 10 in a defined position. For this purpose, the treatment head receptacle 36 is in the form of a cylinder with a recess 37 at one side which ensures that the neck 38 of the treatment head 9 or 10 will be disposed at a defined position when the treatment head is placed in the receptacle 36. A cylindrical pin 39 is introduced into the treatment head initially instead of the selected tool 8, i.e., into the clamping arrangement or shaft receptacle of the treatment head. The cylindrical pin 39 permits further identifying signals to be acquired, as described below.

Figure 8:
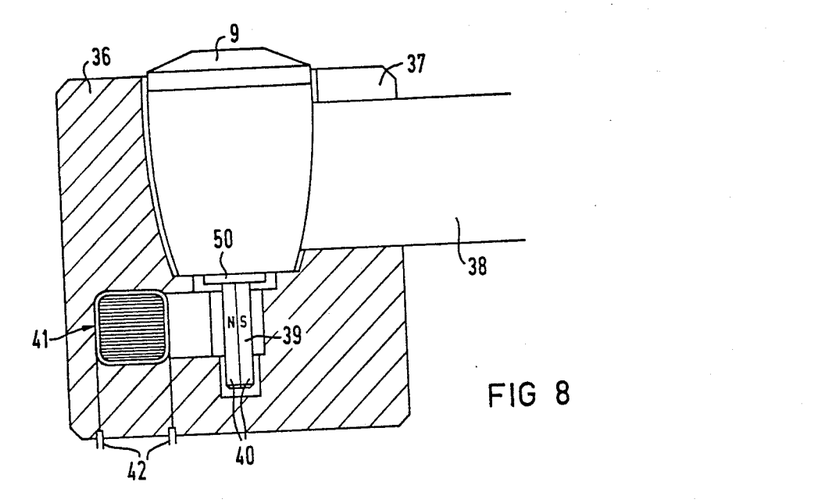
FIG. 8 is a side sectional view of a storage location for the instrument head in the magazine of FIG. 7 in longitudinal section, including a second reader.
Figure 9:
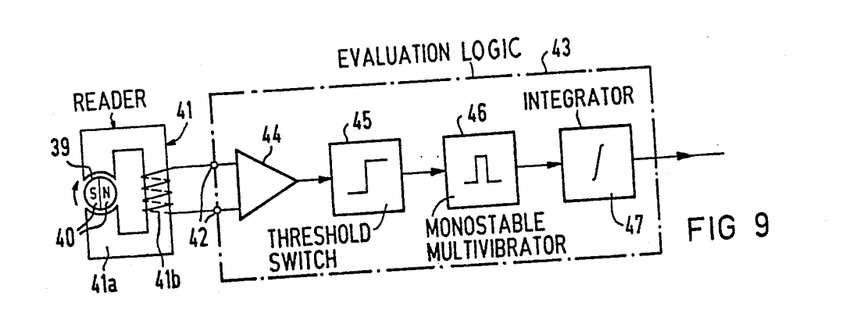
FIG. 9 is a block circuit diagram for the second reader shown in FIG. 8.

The treatment head receptacle 36 functions as a measuring head to acquire data identifying the operating speed at the location of the receptacle 36. One embodiment for this measuring head is shown in sectional view in FIG. 8. In the embodiment of FIG. 8, the pin 39 is cross-magnetized, the magnetization forming two coding elements 40 which interact with a second reader 41 disposed in the region of the magnetic pin 39. The second reader 41 may be a coil arrangement including a core 41a and a coil 41b. Upon rotation of the cross-magnetized pin 39, sinusoidal voltages are generated in a known manner as a consequence of electromagnetic induction, these voltages being tapped at terminals 42, and being supplied to an evaluation unit 43, as shown in the block diagram of FIG. 9. The evaluation unit 43 includes an amplifier 44, a threshold switch 45, a monostable multivibrator 46 and an integrator 47. These components convert the incoming voltage into uniform pulses corresponding to the number of revolutions of the pin 39.

Figure 10:
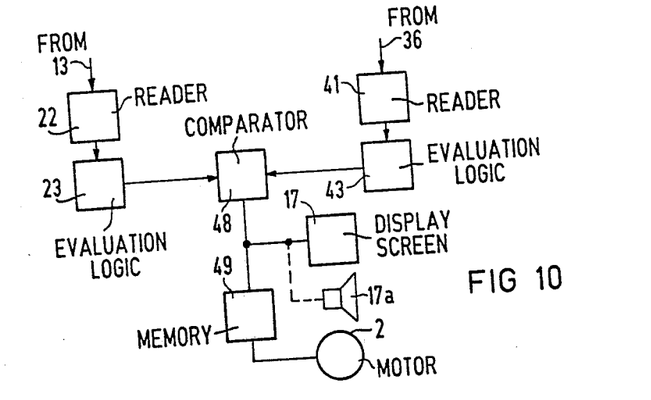
FIG. 10 is a block circuit diagram for both readers in the embodiment shown in FIG. 7.

As shown in the block circuit diagram of FIG. 10, these pulses are supplied to a comparator 48 as the actual value of the rotation speed of the treatment head 9 or 10. The output of the evaluation logic 23 is also supplied to the comparator 48 as a rated speed value.

The cross-magnetized pin 39 thus represents a second coding and the coil arrangement functions as a second reader, to generate data corresponding to one revolution of the pin 39 which are subsequently used for a rated/actual value comparison. As can be seen in FIG. 10 in combination with FIG. 7, the rated value for the comparison is simultaneously obtained from the receptacle 13 in the magazine 15.

Operation of the system based on the aforementioned comparison is as follows. The treatment instrument 1, which contains the drive motor 2, one of the gearing sleeves 5 through 7, and one of the treatment heads 9 or 10, is first provided with the cross-magnetized pin 39 instead of the selected tool 8 which is to be used. The head of the treatment instrument 1, with the magnetic pin 39 inserted therein, is then introduced into the treatment head receptacle 36, as shown in FIG. 8. The tool 8, which is to be used to conduct the treatment, is simultaneously introduced into the receptacle 13. The drive motor 2 is then turned on, and is increased in speed until the rated value and actual value coincide, as determined by the rated/actual value comparison.

If, for example, the comparator 48 is supplied with identifying signals on the basis of the coding of the tool 8 which correspond to a rated speed of, for example, 100,000 rpm, the drive motor 2 is accelerated until the speed at the magnetization pin 39 corresponds to this rated speed. When the rated and actual values coincide, this value is stored in a memory 49. Given further use of the drive, when the tool 8 is introduced into the treatment head 9 or 10 in place of the pin 39, this stored value functions to set the motor speed and thus limits the maximum possible operating speed of the tool.

The rated/actual value comparison insures that a selected tool can never be operated with an impermissible high speed, i.e., a limitation on the operating speed is established dependent on the tool which is selected for use. If, for example, a tool optimally operable at a low speed has been selected and a combination of gearing sleeve and treatment head for a high speed has been selected, the maximum available speed obtainable by the gearing sleeve and treatment head is not reached, rather, its speed is limited to the speed allocated to the selected tool. Conversely, if a tool optimally useable at a very high speed is selected and a gear sleeve and treatment head combination for low-revolution tools is used, the actual value does not reach the prescribed rated value. In this case, an indicator at the display screen 17, such as a flashing light or an audible warning tone, can inform the user of a gearing combination in the treatment instrument which, although not be harmful to the tool or the patient, is inefficient. The magazine 15 in the embodiment of FIG. 7 may for this purpose be provided with a grill for a speaker 17a, the speaker 17a being supplied with an output signal from the comparator 48, as shown in FIG. 10.

Instead of using the cross-magnetized pin 39, the shaft 50 which is used to receive the pin 39 (and subsequently receives the selected tool) may itself be cross-magnetized, or a clamping arrangement received in the hollow shaft 50 may be cross-magnetized, in the manner set forth above. Tests have shown that it is sufficient to merely bring the end face of the treatment head into proximity with the coil 41 to acquire the identifying signals.

Figures 11, 12, 13, 14:
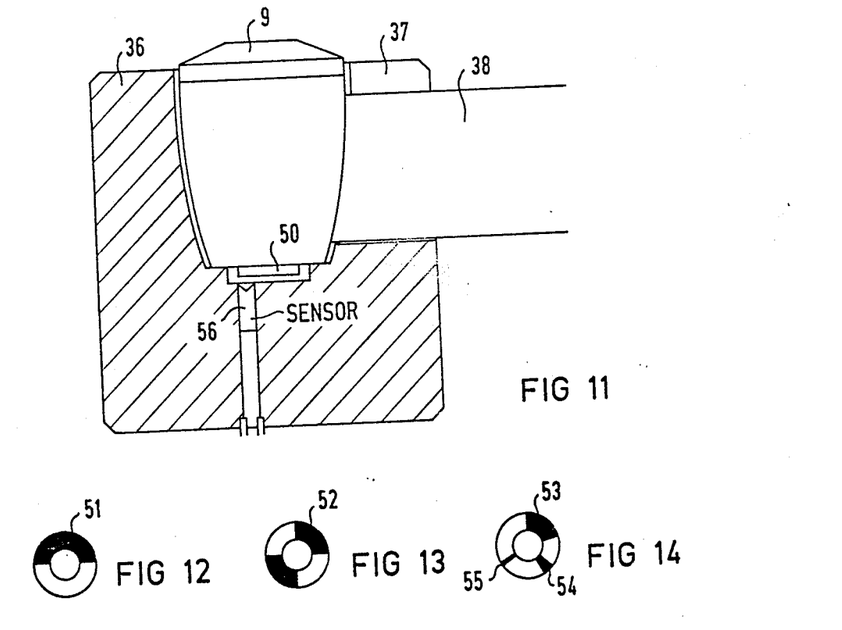
FIG. 11 is a side sectional view of a further embodiment of the treatment instrument receptacle in a system constructed in accordance with the principles of the present invention.
FIGS. 12, 13 and 14 are plan views of various coding elements usable in the embodiment of FIG. 11.

It is also possible to use optical coding instead of the magnetic coding described above. Such an embodiment is shown in FIGS. 11 through 14. In this embodiment, the hollow shaft 50 has one or more optical markings 51 through 55 disposed on the circumference thereof. The markings 51 through 55 are read by an optical sensor element 56 disposed at a suitable location in the treatment head receptacle head 36 adjacent to the end face of the hollow shaft 50. As shown in FIGS. 12 and 13, the markings can be symmetrically arranged, or as shown in FIG. 14 the markings can be asymmetrically arranged. The marking 51 in the embodiment of FIG. 12 supplies one pulse per revolution of the hollow shaft 50, whereas the coding 52 in FIG. 13 provides data which is a multiple of the rotational speed. The asymmetrical coding 53, 54 and 55 of FIG. 14 has the advantage that the marking itself is in turn uniquely identified, so that it can only be read with a specifically designed reader.

Processing of the acquired information in the embodiment of FIG. 11 is undertaken in the same manner as described above in connection with the magnetic embodiment.

It is not necessary that the treatment head receptacle 36 and the coil arrangement 41 be provided in the same magazine with the receptacle 13, however, simplified operation is achieved when this is done.

Although modifications and changes may be suggested by those skilled in the art it is the intention of the inventors to embody within the patent warranted hereon all changes and modifications as reasonably and properly come within the scope of their contribution to the art.

We claim as our invention:

1. In a dental treatment station having a drive unit, a plurality of tools for dental treatment, each tool operable at a respective optimum rotational speed, and means for coupling a selected one of said tools to said drive unit to rotate said selected tool, a tool speed recognition system comprising:

coding means on each tool for identifying the respective optimum rotational speed associated with the tool by encoded data;

means for reading said encoded data on said selected tool and generating an output signal corresponding to said encoded data; and evaluation means for converting said output signal from said means for reading into a control signal for said drive unit to operate the selected tool at its optimum rotational speed.

2. The speed recognition system of claim 1, further comprising means for informing a user, and wherein said evaluation means includes means for converting said output signal from said means for reading into a signal for said means for informing a user to identify to said user said optimum speed for said selected tool.

3. A speed recognition system as claimed in claim 2, wherein said means for informing is an optical display.

4. A speed recognition system as claimed in claim 2, wherein said means for informing is a means for generating a voice output.

5. The speed recognition system of claim 1, wherein said means for coupling a selected one of said tools to said drive unit includes a plurality of treatment heads having different transmission ratios and a plurality of gearing sleeves having different transmission ratios with a selected one of said treatment heads and a selected one of said gearing sleeves being used in combination to couple said selected tool to said drive unit, and wherein said evaluation means includes means for generating a signal identifying a combination of one of said treatment heads and one of said gearing sleeves having, in combination, a transmission ratio best suited to operate said selected tool at its optimum speed.

6. A speed recognition system as claimed in claim 5, further comprising means for informing a user of said one of said treatment heads and said one of said gearing sleeves which are best suited in combination for operating said selected tool at its optimum speed.

7. A speed recognition system as claimed in claim 6, wherein said means for informing said user is a means for generating a visual display identifying said one of said treatment heads and said one of said gearing sleeves.

8. A speed recognition system as claimed in claim 7, wherein said means for generating a visual display is a means for generating a graphic display of said one of said treatment heads and one of said gearing sleeves.

9. A speed recognition system as claimed in claim 7, wherein said means for generating a visual display is a means for generating a textual description of one of said treatment heads and one of said gearing sleeves.

10. A speed recognition system as claimed in claim 6, wherein said means for informing a user is a means for generating a voice description of said one of said treatment heads and said one of said gearing sleeves.

11. A speed recognition system as claimed in claim 1, further comprising means responsive to said control signal for informing a user of the speed of said drive unit.

12. A speed recognition system as claimed in claim 11, wherein said drive unit has a maximum speed, and wherein said means for informing a user of the speed of said drive unit is a means for identifying the speed of said drive unit to a user as a percentage of said maximum speed.

13. A speed recognition system as claimed in claim 1, wherein said coding means on each tool is a binary coding means.

14. A speed recognition system as claimed in claim 1, wherein said plurality of tools includes a tool operable at a lowest optimum speed and a tool operable at a highest optimum speed, and wherein the range of speeds between said lowest speed and said highest speed is divided into a plurality of speed levels, wherein said coding means includes a plurality of coding elements respectively corresponding to said speed levels, and wherein said means for reading includes a plurality of sensors corresponding to said plurality of speed levels and coding elements, said sensors generating parallel signals respectively identifying the presence or absence of a coding element on said selected tool for each speed level.

15. A speed recognition system as claimed in claim 14, wherein each of said speed levels is subdivided into a plurality of sub-levels, and wherein said coding elements of said coding means corresponding to one of said speed levels are respectively positioned on said selected tool at unique locations corresponding to each of said speed sub-levels.

16. A speed recognition system as claimed in claim 14, wherein each of said sensors is an opto-electronic sensor.

17. A speed recognition system as claimed in claim 1, wherein said plurality of tools includes a tool operable at a lowest optimum speed and a tool operable at a highest optimum speed, and wherein the range of speeds between said lowest speed and said highest speed is divided into a plurality of speed levels, wherein said coding means includes a plurality of coding elements respectively corresponding to said speed levels, and wherein said means for reading including one sensor for generating serial signals identifying the presence or absence of each of said coding elements.

18. A speed recognition system as claimed in claim 17, wherein each of said speed levels is subdivided into a plurality of sub-levels, and wherein said coding elements of said coding means corresponding to one of said speed levels are respectively positioned on said selected tool at unique locations corresponding to each of said speed sub-levels.

19. A speed recognition system as claimed in claim 17, wherein said sensor is an opto-electronic sensor.

20. A speed recognition system as claimed in claim 1, wherein said coding means is a bar code on each tool.

21. A speed recognition system as claimed in claim 20, wherein each tool has a shaft having a rotational axis, and wherein said bar code is disposed on said shaft transversely relative to said rotational axis.

22. A speed recognition system as claimed in claim 21, wherein said bar code consists of a plurality of transverse rings on said shaft.

23. A speed recognition system as claimed in claim 21, wherein said means for reading includes a housing having a receptacle adapted to receive said shaft of said tool, and means for initiating reading of said encoded data when said shaft is fully inserted in said receptacle.

24. A speed recognition system as claimed in claim 20, wherein each tool has a shaft with a rotational axis, and wherein said bar code markings are disposed on said shaft parallel to said rotational axis.

25. A speed recognition system as claimed in claim 24, wherein said means for coupling said selected one of said tools to said drive unit includes a treatment head adapted to receive the shaft of said selected tool, said bar code being disposed on said shaft so that at least a portion thereof is exposed when said shaft is received in said treatment head, and wherein said means for reading includes a housing having a receptacle adapted to receive said selected tool in said treatment head when said treatment head is placed over said receptacle, and means for initiating reading of said encoded data when said treatment head is in place over said receptacle.

26. A recognition system as claimed in claim 1, wherein said means for coupling has a rotating drive output, said control signal corresponding to a rated speed value for said selected tool, said speed recognition system further comprising:
   means at said drive output for generating a signal corresponding to the speed of said drive output;
   means connected to said means for generating a signal for converting said signal into an actual speed value signal;
   means for comparing said rated value signal with said actual value signal to generate a comparison signal; and
   means responsive to said comparison signal for operating said drive unit at a speed so that the speed of said drive output equals said rated value.

27. A speed recognition system as claimed in claim 26, wherein said means for generating a signal corresponding to the speed of said drive output comprises:
   means at said drive output for generating a varying signal during each revolution of said drive output; and
   means for reading said varying signal and generating an output signal which is said signal corresponding to the speed of said drive output.

28. A recognition system as claimed in claim 27, wherein said means for coupling has a treatment head on which said drive output is disposed, and wherein said means for reading said varying signal includes a housing having a receptacle adapted to receive said treatment head.

29. A recognition system as claimed in claim 27, wherein said means for generating a varying signal is a cross-magnetized pin in said drive output and wherein said means for reading said varying signal is a means for magnetically reading said varying signal.

30. A recognition system as claimed in claim 27, wherein said drive output has an output face and wherein said means for generating a varying signal is at least one optically readable mark on said face, and wherein said means for reading said varying signal is a means for optically reading said varying signal.

31. A speed recognition system as claimed in claim 30, wherein said means for generating said varying signal is a plurality of optically readable marks symmetrically disposed on said face.

32. A speed recognition system as claimed in claim 30, wherein said means for generating said varying signal is a plurality of optically readible marks asymmetrically disposed on said face.

33. In a dental treatment station having a drive unit, a plurality of tools for dental treatment, each tool operable at a respective optimum rotational speed, a plurality of gearing sleeves having respective transmission ratios, and a plurality of treatment heads having respective transmission ratios, one of said gearing sleeves and one of said treatment heads being used in combination to couple a selected one of said tools to said drive unit to rotate said tool, a speed recognition system comprising:
   coding means on each tool for identifying the respective optimum speed associated with the tool by encoded data;
   a housing;
   a receptacle in said housing adapted to receive said selected one of said tools before coupling said selected tool to said drive unit, said encoded data being disposed in said receptacle when said selected tool is received therein;
   means disposed at said receptacle for reading the encoded data on a tool in the receptacle and generating an output signal corresponding to the encoded data;
   an evaluation unit including means for converting said output signal from said means for reading into a control signal and means for identifying one of said gearing sleeves and one of said treatment heads best suited for use in combination to operate said selected tool at its optimum speed and generating a display signal corresponding thereto;
   means connected to said evaluation unit responsive to said control signal to operate said drive unit to rotate said selected tool at its optimum speed; and
   display means connected to said evaluation unit responsive to said display signal to inform a user of said one of said gearing sleeves and said one of said treatment heads best suited to operate said selected tool and of said optimum speed for said selected tool.

34. A speed recognition system as claimed in claim 33, wherein said means for displaying is a means for optically displaying.

35. A speed recognition system as claimed in claim 33, wherein said means for displaying is a means for audibly displaying.

36. A speed recognition system as claimed in claim 33, wherein said means for displaying is a part of said housing.

37. In a dental treatment station having a drive unit, a plurality of tools for dental treatment, each tool operable at a respective optimum rotational speed, and means for coupling a selected one of said tools for use in treatment to said drive unit, said means for coupling having a drive output, a speed recognition system comprising:
   coding means on each tool for identifying the respective optimum speed associated with the tool by encoded date;
   a housing;
   a first receptacle in said housing adapted to receive said selected tool before treatment, said coding means on said selected tool being disposed in said receptacle when said selected tool is received therein;
   means for reading said encoded data on said selected tool in said receptacle and generating an output signal corresponding to said encoded data;
   means for converting said output signal into a rated speed value for said selected tool;
   means at said drive output for generating a varying signal during each revolution of said drive output;
   a further receptacle in said housing adapted to receive at least said drive output of said means for coupling;
   means in said further receptacle for receiving said varying signal from said drive output and generating an output signal;
   means for converting said output signal from said means for receiving into an actual speed value signal for said drive output;
   means for comparing said rated speed value signal to said actual speed value signal to generate a control signal; and
   means responsive to said control signal to operate said drive unit at a speed so that the speed of said drive output equals said rated speed value.

* * * * *